US00PP12620P2

(12) United States Plant Patent
Clark et al.

(10) Patent No.: US PP12,620 P2
(45) Date of Patent: May 14, 2002

(54) NECTARINE TREE-NAMED 'BRADLEY' CULTIVAR

(75) Inventors: John Reuben Clark; James Norman Moore, both of Fayetteville, AR (US)

(73) Assignee: University of Arkanas, Fayetteville, AR (US)

( * ) Notice: Subject to any disclaimer, the term of this patent is extended or adjusted under 35 U.S.C. 154(b) by 10 days.

(21) Appl. No.: 09/687,120

(22) Filed: Oct. 13, 2000

(51) Int. Cl.[7] ..... A01H 5/00
(52) U.S. Cl. ..... Plt./190

(58) Field of Search ..... Plt./190

*Primary Examiner*—Bruce R. Campell
*Assistant Examiner*—A Para

(57) ABSTRACT

Description and specifications of a new and distinct nectarine tree variety which originated from an $F_2$ population of seed produced by a hand pollinated cross of Arkansas Peach Selection 190 (non-patented) and Arkansas Nectarine Selection 178 (non-patented) is provided. This new nectarine variety can be distinguished by its large, attractive, very firm fruit, good yielding abilities, good storage and shipping characteristics, and high levels of genetic resistance to the disease bacterial spot.

3 Drawing Sheets

SUMMARY OF THE INVENTION

The new and distinct variety of nectarine originated from an $F_2$ population of a hand pollinated cross of Arkansas Peach Selection 190 (non-patented)×Arkansas Nectarine Selection 178 (non-patented) made in 1980 at the Arkansas Agricultural Experiment Station Fruit Substation at Clarksville, Ark. The parent plants used in this hybridization have not been named and released and are unavailable in commerce.

Plants and fruit of this new variety differ phenotypically from its parents. The new variety is earlier ripening and possesses glabrous fruit with more red skin color and better flavor than the pubescent fruit of the parent Arkansas Peach Selection 190, and is later ripening, has larger fruit and is more productive than the parent Arkansas Nectarine Selection 178. The new variety produces more attractive and more flavorful fruit than either of its parents. Both the parents and the instant variety are the genus and species *Prunus persica*.

The $F_2$ seeds resulting from this controlled hybridization were germinated in a greenhouse in the spring of 1985 and planted in a field on the Arkansas Agricultural Experiment Station in Clarksville, Ark. The seedlings fruited during the summer of 1988 and one, designated Arkansas 402, was selected for its large, firm, attractive fruits, and healthy, bacterial spot-resistant plants. During 1988, the original plant selection was propagated asexually, at the above noted location, by budding onto standard peach rootstock variety 'Lovell' (non-patented) and a test plot of two plants was established. Subsequently, larger test plantings have been established with asexually multiplied plants (propagated at the same location) at two additional locations in Arkansas (Clarksville and Hope, Ark.).

The new variety has been asexually multiplied several times since 1988 at this location by budding onto each rootstock variety 'Lovell' and no incompatibility with peach rootstock has occurred following budding. During all asexual multiplication, the characteristics of the original plant have been maintained and no aberrant phenotypes have appeared.

Plants of the new variety are moderately vigorous and are standard in size in comparison to other nectarine or peach trees (*Prunus persica*). Trees are very productive, and show good resistance to infection by bacterial spot, incited by *Xanthomonas campestris* pv. *pruni* (Smith) Dye. The new variety is consistently more resistant to both fruit and leaf infections of bacterial spot than the comparison nectarine varieties 'Redgold' (U.S. Plant Pat. No. 1,329) and 'Summer Beaut' (U.S. Plant Pat. No. 4,093). The new variety blooms in the spring near the same time as the comparison varieties 'Redgold' and 'Summer Beaut'. No winter cold injury has been observed on wood or buds of the new variety in Arkansas tests where minimum temperatures have reached −23° C. Chilling requirement to break dormancy is estimated to be 750 hours below 7° C.

Fruit of the new variety ripens in early midseason, averaging 21 days earlier than the 'Redgold' variety, 5 days earlier than the 'Summer Beaut' variety, and near that of the reference peach variety 'Redhaven' (non-patented). Average ripening date is June 29 in west-central Arkansas. Fruits do not soften rapidly after maturity, and fruit quality is retained well on the tree after maturity for 5 to 7 days. Fruit yields of the new variety have been consistently higher than the 'Redgold' and 'Summer Beaut' varieties at all test locations. Yields are consistent from year to year.

The fruit of the new variety is round in shape, without a prominent tip or bulging suture. Fruits are attractive with light bright red skin color over orange ground color. Fruit finish is good with no blemishes. The fruit skin is medium in thickness and resistant to cracking. The flesh of the fruit is a clear uniform orange color without red pigment. The flesh of the fruit is non-melting in texture and very firm. Mature fruits are much more firm than those of the 'Redgold' and 'Summer Beaut' varieties and storage ability is superior to the standard varieties due to this enhanced firmness. Fruit size is large, averaging 146.4 g, but careful management of crop load is needed to ensure good fruit size.

The fresh fruit rates good in flavor, but exhibits a strong processing peach flavor rather than a typical nectarine flavor. Soluble solids average 11.6%.

The distinctive features of the new variety are its large, attractive, very firm fruits, good yield potential, and its high resistance to fruit and leaf infection by the disease, bacterial spot.

The new variety has been named the 'BRADLEY' cultivar.

BRIEF DESCRIPTION OF THE PHOTOGRAPHS

The accompanying photographs show typical specimens of the fruit (FIGS. 1 and 2) and leaf (FIG. 3) of the new variety in color as nearly true as it is reasonably possible to make in a color illustration of this character.

DETAILED DESCRIPTION OF THE NEW VARIETY

The following is a detailed description of the botanical and pomological characteristics of the subject nectarine. Color data are presented in The Royal Horticultural Society Colour Chart designations and are supplemented with readings from a Minolta Chroma Meter CR-200, version 3.0, which measures absolute chromaticity in tristimulus values L, a, and b. Calibration was performed using a standard white plate supplied by the manufacturer.

Where dimensions, sizes, colors and other characteristics are given, it is to be understood that such characteristics are approximations of averages set forth as accurately as practical.

The descriptions reported herein are from specimens grown at Clarksville, Ark. and are from trees grown in trickle (drip) irrigated orchards growing on a Linker fine sandy loam soil. The data were collected from nine-year old trees of the instant variety except yield data that were taken on five-year-old trees in a replicated test planting.

Tree:

*Size.*—Mature trees (5 years of age and older) average 3.4 m to 3.7 m in height and 4.7 to 5.6 m in spread or width and gave an upright growth habit, as grown on 'Lovell' rootstock using an open-center training system commonly used on nectarines. Tree size is comparable to that of the 'Red Gold' and 'Summer Beaut' varieties.

*Growth.*—Moderately vigorous, symmetrical form, good canopy development.

*Productivity.*—Very good and consistent from year to year. Yield measured 51.5 kg/tree on five-year old trees and exceeded the yield of 'Summer Beaut' of 30.8 kg/tree and 'Red Gold' of 16.7 kg/tree in a test planting of identical age and growing conditions.

*Cold hardiness.*—Wood and dormant buds hardy to −23° C.

*Disease resistance.*—Leaves and fruit resistant to bacterial spot under growing conditions where bacterial spot infection is often very severe on susceptible genotypes. No bactericides were used in the development or evaluation of the instant cultivar. Evidence of bacterial spot infection less than that of 'Red Gold' and 'Summer Beaut' varieties in all years of evaluation. A commercial fungicide program was utilized in orchards used in the development and evaluation of the instant variety, thus no resistance to brown rot or scab, the other common diseases at Clarksville, Ark., was determined.

*Insect resistance.*—Insecticides were applied to orchards used in the development of the instant variety to control the common insects at the location including oriental fruit moth, plum curculio, stinkbug, tarnished plant bud, lesser peach tree borer and greater peach tree borer. Therefore no insect resistance was determined in the testing of the instant variety.

Foliage:

*Shoots.*—Glabrous. Mature shoot length 63.6 cm; diameter base 6.6 mm, midpoint 4.2 mm, terminal 2.7 mm. Mature shoot color adaxial side: Greyed Purple Group (183A), L=35.35, a=20.47, b=9.99; Mature shoot color abaxial side: Yellow Green Group (144A).

*Leaves.*—Simple, alternate, glabrous, lanceolate, petiolate, deciduous. Venation pinnate; base acute to occasional oblique; terminal or apex acuminate; margin serrated. Mature leaf size: length 15.0 cm; diameter midpoint 3.68 cm. Leaf serrations; 6.25/cm. Mature leaf color: Abaxial-Yellow Green Group (147B), L=45.13, a=11.61, b=20.01 and anthocyanin present on the abaxial midrib only (central vein) on mature leaves; Adaxial-Yellow Green Group (147A), L=39.54, a=−8.69, b=13.66 and anthocyanin present on adaxial midrib of mature leaves. Young leaf color: Abaxial-Yellow Green Group (146B), L=51.73, a=−16.60, b=28.90; Adaxial-Yellow Green Group (146A), L=43.79, a=−16.74, b=25.24. Anthocyanin not present on abaxial or adaxial side of young leaves on midrib or other location. Mature leaf pedicel length: 10.3 mm; anthocyanin present on adaxial and abaxial sides of mature leaf petiole and absent on young leaf petiole. Leaf glands: reniform, 5 per leaf, located on basal portion of leaf blade near juncture with petiole. Leaf glands are 0.96 mm in width and 1.35 mm in length and color of glands is Greyed Orange Group (200A). Leaf scar beneath bud at the end of the growing season 3 mm wide.

*Buds.*—Flower buds ovoid in shape; size at the termination of the growing season 3 mm long and 2 mm wide; dormant flower bud color Greyed Orange Group (175 A). Number of leaf buds per 15 cm: 8.3. Number of flower buds per 15 cm: 16.7. Mature shoot internode length: base 5.7 mm, midpoint 4.0 mm, terminal 6.9 mm.

Bark (of mature trunk of tree):

*Color.*—Greyed Orange Group (166A); L=44.32, a=3.66, b=7.02.

Flowers: Bloom occurs prior to vegetative bud break; solitary to occasional double individual flowers at a single node; perfect; self-fertile.

*Date of bloom.*—First, Julian 79 (March 19); Full, Julian 87 (March 27).

*Size.*—Diameter fully open 9.1 mm.

*Type.*—Non-showy.

*Color.*—Red Purple Group (62C), L=90.06, a=25.23, b=0.84.

*Petals per flower.*—5.

*Length of pistil.*—1.38 cm.

*Stamens.*—Numerous with pollen present, fertile and abundant.

Fruit:

*Size.*—Large, avg. 146.4 g; diameter stem end 6.76 cm, equator 7.70 cm, blossom end 6.52 cm; length base to apex 7.54 cm.

*Shape.*—Round, symmetrical, without pronounced tip or suture bulge.

*Skin.*—Glabrous, attractive; ground color Orange Group (25C), L=68.02, a=19.34, b=55.91; overcolor Red Group (46A), L=39.88, a=38.80, b=19.94. Skin medium thick and tenacious to flesh.

*Flesh.*—Color: Orange Group (25C), L=68.03, a=10.57, b=53.31; uniform throughout; clingstone; non-melting texture; very firm; no tendency to crack or split. Firmness when measured by a fruit pressure tester (using a McCormick model FT327 fruit pressure tester, 11 mm diameter probe, McCormick Fruit Tree Co., Yakima, Wash.) had average firmness value of 5.2 kg. Quality good, with pronounced processing peach flavor and aroma.

*Pedicel length.*—7.4 mm.

*Ripe date.*—June 29 (Julian 181) in west-central Arkansas. Ripening of individual fruit is uniform.

*Tendency of pit to split.*—Variable among years with no split pits most years up to a a maximum of 20% split pits measured.

*Soluble solids.*—11.6%.

*pH.*—3.4 (of undiluted juice extracted from fruit).

Pit/stone:

*Size.*—Length 4.08 cm; diameter (midpoint) 2.43 cm.

*Shape.*—Oblong with deep furrowing and pitting.

*Color.*—Greyed Orange Group (164A), L=61.54, a=19.23, b=39.62.

Kernel:

*Size.*—Length 16.6 mm; width 9.3 mm; diameter varies with dryness of the kernel but is up to 2 mm.

*Shape.*—Elliptical with a straight or slightly curved apiculate apex.

*Color.*—Greyed Orange Group (164A).

Uses: Fresh consumption, canned, frozen; not evaluated for drying or other uses.

The variety: The most distinctive features of the variety are its large, attractive, very firm fruits, good yield potential and its high resistance to both foliar and fruit infection by the disease bacterial spot.

We claim:

1. A new and distinct variety of nectarine, substantially as illustrated and described, characterized by its large, attractive, very firm fruits, good productivity, good storage and shipping characteristics, and high levels of resistance to bacterial spot.

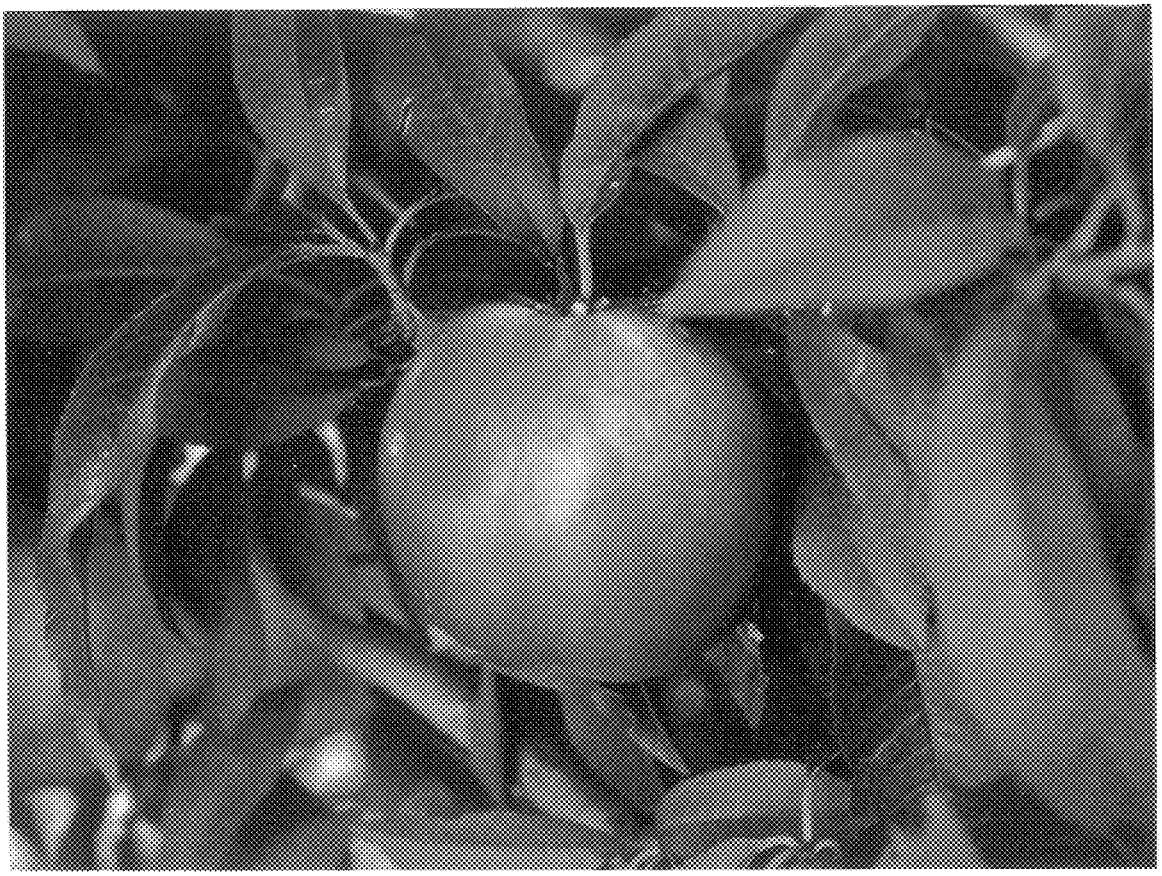

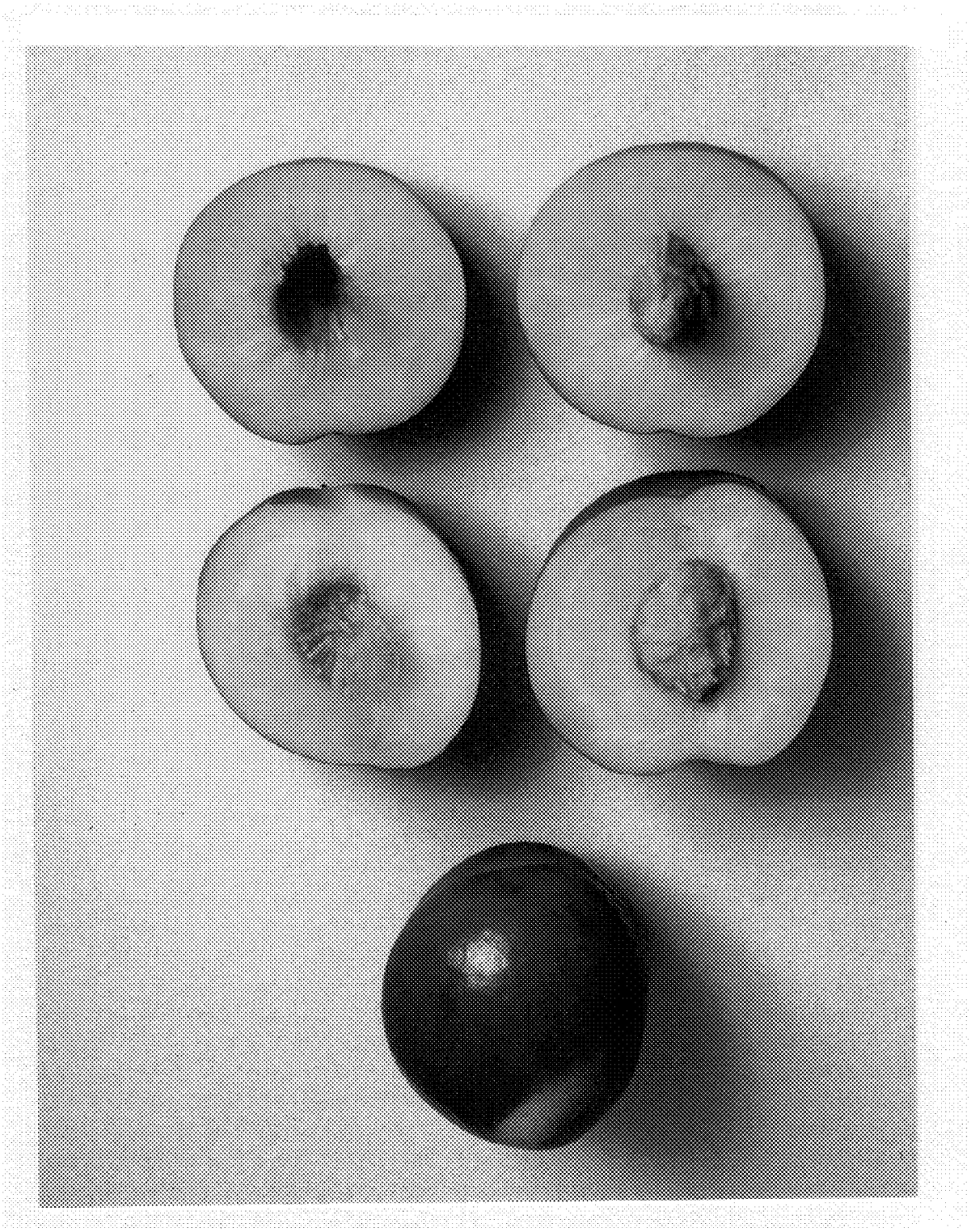

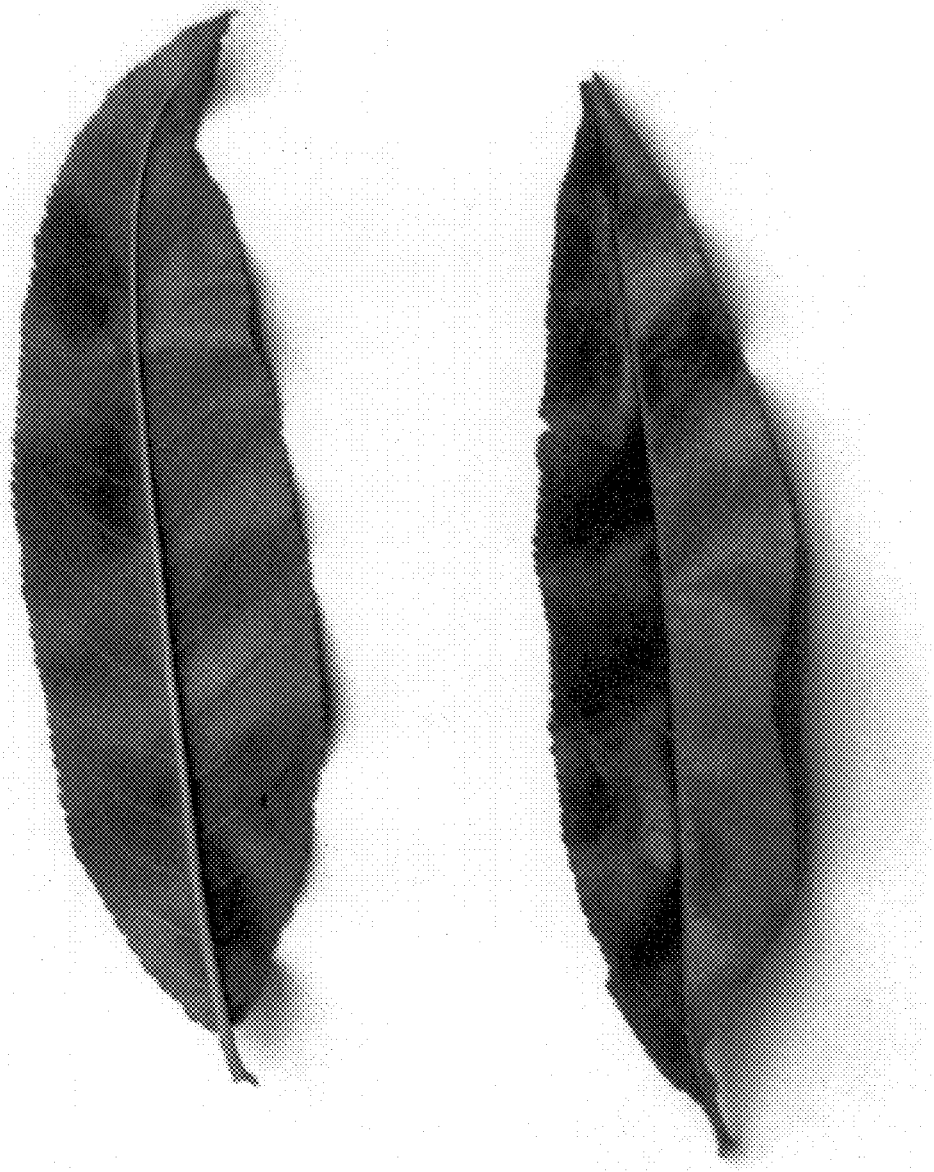

* * * * *